United States Patent [19]

Dean et al.

[11] Patent Number: 4,826,673
[45] Date of Patent: May 2, 1989

[54] METHODS AND COMPOSITIONS FOR ENHANCING MAGNETIC RESONANCE IMAGING

[75] Inventors: Richard T. Dean; Youlin Lin, both Chesterfield; Robert W. Weber, Manchester; David H. White, Florissant, all of Mo.

[73] Assignee: Mallinckrodt, Inc., St. Louis, Mo.

[21] Appl. No.: 689,825

[22] Filed: Jan. 9, 1985

[51] Int. Cl.$^4$ .................. A61K 49/00; A61B 5/05; A61B 6/00
[52] U.S. Cl. .................................. 424/9; 128/653; 128/654; 436/173; 436/806; 514/492; 514/501; 514/502; 514/505; 534/15; 534/16; 556/45; 556/57; 556/138; 562/564; 562/565
[58] Field of Search ............... 562/564; 534/565, 15, 534/16; 260/429 J; 436/806, 173; 424/2, 4, 9; 128/653'654; 556/1, 42, 45, 51, 57, 64, 110, 118, 136, 138; 514/492, 499, 501, 502, 505

[56] References Cited

U.S. PATENT DOCUMENTS

| 3,650,963 | 3/1972 | Werdehausen et al. | 562/565 X |
| 4,352,751 | 10/1982 | Wieder et al. | 562/565 X |
| 4,647,447 | 3/1987 | Gries | 424/9 |
| 4,687,659 | 8/1987 | Quay | 424/9 |

FOREIGN PATENT DOCUMENTS

| 0849054 | 1/1961 | France | 562/565 |
| 0742996 | 1/1956 | United Kingdom | 562/565 |

OTHER PUBLICATIONS

Weinmann et al., AJR, vol. 142, (1984), pp. 619–624.

Primary Examiner—Robert J. Warden
Assistant Examiner—Stephen C. Wieder
Attorney, Agent, or Firm—Senniger, Powers, Leavitt and Roedel

[57] ABSTRACT

The disclosure is directed to compounds of the formula:

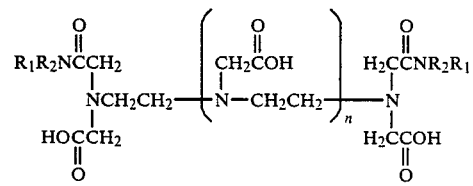

wherein n=0, 1, 2, 3 or 4, and $R_1$ and $R_2$ may be the same or different and are selected from the group consisting of hydrogen and lower alkyl and hydroxy lower alkyl groups containing between 1 and 6 carbon atoms. Complexes of iron(II), iron(III), manganese(II), manganese(III), gadolinium(III), chromium(III), cobalt(II), and nickel(II) and such compounds are useful for enhancing magnetic resonance images of body organs and tissues. Illustrative complexes include (N,N''-bis[N-(2,3-dihydroxypropyl) carbamoylmethyl]diethylenetriamine-N,N',N''-triaceto)-iron(III), (N,N''-bis[N-(2,3-dihydroxypropyl)carbamoylmethyl]diethylenetriamine-N,N',N''-triaceto)manganese(II), (N,N''-bis[N-(2,3-dihydroxypropyl) )carbamoylmethyl]diethylenetriamine-N,N',N''-triaceto)gadolinium(III) and (N,N'-bis[N-(2,3-dihydroxypropyl)-carbamoylmethyl]ethylenediamine-N,N'-diaceto)manganese(II).

22 Claims, No Drawings

METHODS AND COMPOSITIONS FOR ENHANCING MAGNETIC RESONANCE IMAGING

BACKGROUND OF THE INVENTION

This invention relates to magnetic resonance imaging (MRI), also referred to as nuclear magnetic resonance (NMR) imaging, and more particularly, to methods and compositions for enhancing magnetic resonance images of body organs and tissues.

The recently developed techniques of MRI or NMR imaging encompass the detection of certain atomic nuclei utilizing magnetic fields and radio-frequency radiation. It is similar in some respects to x-ray computed tomography (CT) in providing a cross-sectional display of the body organ anatomy with excellent resolution of soft tissue detail. In current use, the images produced constitute a map of the distribution density of protons and/or their relaxation times in organs and tissues. The MRI technique is advantageously non-invasive as it avoids the use of ionizing radiation.

While the phenomenon of NMR was discovered in 1945, it is only relatively recently that it has found application as a means of mapping the internal structure of the body as a result of the original suggestion of Lauterbur (Nature, 242, 190–191, 1973). The lack of any known hazard associated with the level of the magnetic and radio-frequency fields that are employed renders it possible to make repeated scans on vulnerable individuals. Additionally, any scan plane can readily be selected including transverse, coronal, and sagittal sections.

In an NMR experiment, the nuclei under study in a sample (e.g. protons) are irradiated with the appropriate radio-frequency (RF) energy in a highly uniform magnetic field. These nuclei as they relax subsequently emit RF radiation at a sharp resonant frequency. The emitted frequency (RF) of the nuclei depends on the applied magnetic field.

According to known principles, nuclei with appropriate spin when placed in an applied magnetic field [B, expressed generally in units of gauss or tesla ($10^4$ gauss)] align in the direcion of the field. In the case of protons, these nuclei precess at a frequency $f = 42.6$ MHz at a field strength of 1 Tesla. At this frequency, an RF pulse of radiation will excite the nuclei and can be considered to tip the nuclei out of the field direction, the extent of this rotation being determined by the pulse duration and energy. After the RF pulse, the nuclei "relax" or return to equilibrium with the magnetic field, emitting radiation at the resonant frequency. The decay of the signal is characterized by two relaxation times, i.e., $T_1$, the spin-lattice relaxation time or longitudinal relaxation time, that is, time taken by the nuclei to return to equilibrium along the direction of the externally applied magnetic field, and $T_2$, the spin-spin relaxation time associated with the dephasing of the initially coherent precession of individual proton spins. These relaxation times have been established for various fluids, organs and tissues in different species of mammals.

In MRI, scanning planes and slice thickness can be selected without loss of resolution. This permits high quality transverse, coronal and sagittal images to be obtained directly. The absence of any moving parts in MRI equipment promotes a high reliability. It is believed that MRI or NMR imaging has a greater potential than CT for the selective examination of tissue characteristics in view of the fact that in CT, x-ray attenuation coefficients alone determine image contrast whereas at least four separate variables ($T_1$, $T_2$, nuclear spin density and flow) may contribute to the NMR signal. For example, it has been shown (Damadian, Science, 171, 1151, 1971) that the values of the $T_1$ and $T_2$ relaxation in tissues are generally longer by about a factor of 2 in excised specimens of neoplastic tissue compared with the host tissue.

By reason of its sensitivity to subtle physio-chemical differences between organs and/or tissues, it is believed that MRI may be capable of differentiating tissue types and in detecting diseases which induce physio-chemical changes that may not be detected by x-ray or CT which are only sensitive to differences in the electron density of tissue. The images obtainable by MRI techniques also enable the physician to detect structures smaller than those detectable by CT and thereby provide comparable or better spatial resolution.

Continuing efforts are being made to develop imaging agents for enhancing the images obtained through the use of MRI techniques.

SUMMARY OF THE INVENTION

Among the several objects of the invention may be noted the provision of novel complexes of certain ligands with one or more central metal ions for use in enhancing magnetic resonance images of body organs and tissues; the provision of such metal complexes which exhibit favorable toxicity profiles; and the provision of methods for enhancing magnetic resonance images of body organs and tissues through the administration of such complexes. Other objects and features will be in part apparent and in part pointed out hereinafter.

Briefly, the invention is directed to compounds of the formula:

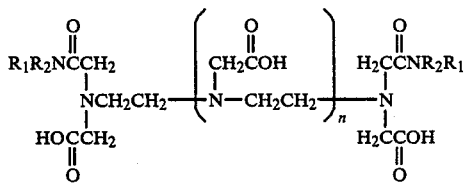

wherein n=0, 1, 2, 3 or 4, and $R_1$ and $R_2$ may be the same or different and are selected from the group consisting of hydrogen and lower alkyl and hydroxy lower alkyl groups containing between 1 and 6 carbon atoms, and complexes of such compounds and one or more central metal ions which may be iron (II), iron(III), manganese(II), manganese(III), gadolinium(III), chromium(III), cobalt(II) or nickel(II). The invention is also directed to methods for enhancing magnetic resonance images of body organs and tissues by administering such complexes to a mammal in sufficient amounts to provide enhancement of magnetic resonance images of the body organs and tissues.

DESCRIPTION OF THE PREFERRED EMBODIMENTS

In accordance with the present invention, it has now been found that magnetic resonance images of body organs and tissues may be usefully enhanced through the administration to a mammal of substantially non-toxic metal complexes of compounds of the formula:

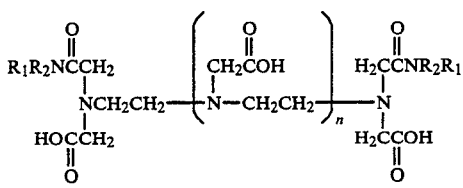

wherein n=0, 1, 2, 3 or 4, and $R_1$ and $R_2$ may be the same or different and are selected from the group consisting of hydrogen and lower alkyl and hydroxy lower alkyl groups containing between 1 and 6 carbon atoms.

Complexes of the novel ligands or compounds of the above class with one or more central metal ions such as iron(II), iron(III), manganese(II), manganese(III), gadolinium(III), chromium(III), cobalt(II) and nickel-(II) are useful for enhancing magnetic resonance images. While such metal ions are themselves paramagnetic in nature and capable of altering the magnetic resonance signal characteristics of body tissues, organs or fluids, they may undesirably exhibit significant toxicity when administered in the form of ionic salts. However, we have found that the novel complexes of the present invention are relatively or substantially nontoxic and are therefore useful for enhancing magnetic resonance images by favorably altering relaxation times $T_1$ and $T_2$ and thereby affording improved contrast between normal and diseased tissues or organs.

The preferred complexes of the invention are those formed from the above ligands and iron(II), iron(III), manganese(II), manganese(III) and gadolinium(III) as the central metal ion or ions. Depending upon the particular ligand employed and the particular central metal ion used, the complexes formed may be neutral, nonionic or zwitterionic in nature or they may be negatively charged. The former complexes are preferred and appear to exhibit relatively lower toxicity as compared to ionic or negatively charged complexes. The negatively charged complexes formed by the ligands and central metal ions enumerated above may be further complexed with one or more cations of an inorganic or organic base which are physiologically tolerated such as sodium, potassium, calcium, N-methylglucamine or diethanolamine.

The preferred ligands are those in which n=0, 1 or 2, $R_1$ is hydrogen or lower alkyl (e.g. methyl) and $R_2$ is 2,3-dihydroxypropyl, 2-hydroxyethyl, 1-hydroxymethyl-2-hydroxyethyl, 1-hydroxymethyl-2,3-dihydroxypropyl and hydroxymethyl. Illustrative novel ligands of the above formula include N,N''-bis[N-(2,3-dihdroxypropyl)carbamoylmethyl]diethylenetriamine-N,N',N''-triacetic acid, N,N'-bis[N-(2,3-dihydroxypropyl)carbamoylmethyl]ethylenediamine-N,N'-diacetic acid, N,N'''-bis[N-(2-hydroxyethyl)carbamoylmethyl]triethylenetetraamine-N,N',N'',N'''-tetraacetic acid, N,N''-bis[N-(1-hydroxymethyl-2,3-dihydroxypropyl)carbamoylmethyl]diethylenetriamine-N,N',N''-triacetic acid and N,N'-bis[N-(2-hydroxyethyl)carbamoylmethyl]ethylenediamine-N,N'-diacetic acid. As shown by the working examples set forth hereinafter, the ligands may be formed by reacting the appropriate anhydride precursor compound with an amino hydroxy alkane to yield the desired compound.

Illustrative complexes of such ligands and one or more central metal ions from the group consisting of iron(II), iron(III), manganese(II), manganese(III), gadolinium(III), chromium(III), cobalt(II) and nickel-(II) include (N,N''-bis[N(2,3-dihydroxypropyl)carbamoylmethyl]diethylenetriamine-N,N',N''-triaceto)iron(III), (N,N''-bis[N-(2,3-dihydroxypropyl)carbamoylmethyl]diethylenetriamine-N,N',N''-triaceto)manganese(II), (N,N''-bis[N-(2,3-dihydroxypropyl)carbamoylmethyl]diethylenetriamine-N,N',N''-triaceto)gadolinium(III), (N,N'-bis[N-(2,3-dihydroxypropyl)carbamoylmethyl]ethylenediamine-N,N'-diaceto)manganese(II) and (N,N'-bis[N-(2-hydroxyethyl)carbamoylmethyl]ethylenediamine-N,N'-diaceto)iron(II). The complexes are formed by reacting the ligand with a metal salt or oxide, the metal being complexed as central metal ions with the carboxylic acid groups of the ligand.

As shown by the toxicity studies set forth hereinafter, representative metal complexes of the invention possess favorable intravenous toxicity profiles and have $LD_{50}$ values ranging from approximately 5.9 mmol/kg to approximately 12.4 mmol/kg, as compared with an $LD_{50}$ of approximately 7.2 mmol/kg for the paramagnetic chelate disodium (diethylenetriaminepentaaceto)gadolinium(III), (GdNa$_2$DTPA), a relatively safe agent for use in magnetic resonance imaging. They also favorably influence relaxation times.

The substantially nontoxic metal complexes of the present invention are administered to a mammal in a sufficient amount to provide enhancement of magnetic resonance images of body organs and tissues prior to obtaining a magnetic resonance scan or scans of such organs and tissues with "slices" being taken at the level of the desired organ at various time periods post-administration. The complexes of the invention may also be used as x-ray contrast agents.

The following examples illustrate the practice of the invention.

EXAMPLE 1

Preparation of
N,N''-Bis[N-(2,3-dihydroxypropyl)-carbamoylmethyl]-diethylenetriamine-N,N',N''-triacetic Acid

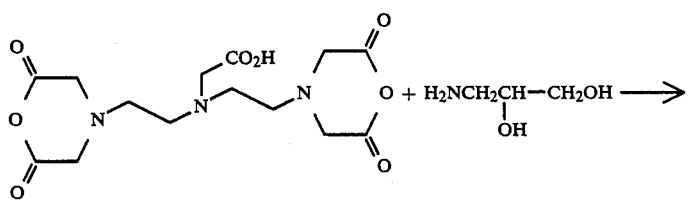

1

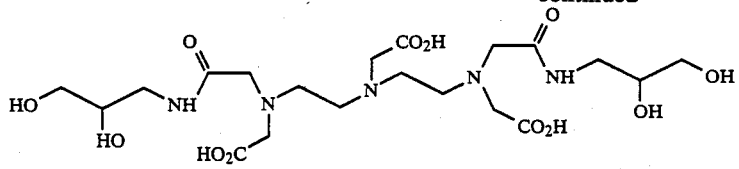

To a solution of 3-amino-1,2-propanediol (15.94 g., 0.175 mol) in anhydrous methanol (100 ml) was added anhydride (1) (17.87 g., 0.05 mol) in portions, maintaining internal temperature at −30° C. by cooling in an ice bath. The resulting mixture was stirred for 24–48 hr at room temperature. The solvent was then removed via aspirator to give 37.6 g. of a yellow syrup. Further purification was carried out on 15.0 g. of this crude product by dissolving the syrup in a 1:1 methanol/water solution (50 ml) and passing the solution through 150 ml of "Amberlite IR 120 H.C.P." resin (prewashed with 500 ml water, then 300 ml 1:1 methanol/water) using 1:1 methanol/water as eluent. Evaporation of pure fraction gave 5.79 g. of the desired compound (2) as a clear glass, with a $^{13}C$ NMR spectrum consistent for the assigned structure.

Analysis: Calculated for $C_{20}H_{37}N_5O_{12} \cdot H_2O$: C; 43.08; H, 7.05; N, 12.56. Found: C, 42.94; H, 6.52; N, 12.21.

EXAMPLE 2

Preparation of (N,N'''-Bis[N-(2,3-dehydroxypropyl)-carbamoylmethyl]deithylenetriamine-N,N'N''-triaceto)gadolinuium-(III)

To a solution of the ligand N,N'''-bis[N-(2,3-dihydroxypropyl)carbamoylmethyl]diethylenetriamine-N,N',N''-triacetic acid (2) (5.49 g., 0.0102 mol) in water (220 ml) was added gadolinium oxide (1.85 g., 0.0051 mol). The resulting mixture was heated at 80° C. for 16 hr. After cooling to room temperature, the solution was filtered through a 0.45μ Millipore filter and evaporated under reduced pressure to give the gadolinium(III) complex (3) as a slightly yellow glass.

Analysis: Calculated for $C_{20}H_{34}N_5O_{12}Gd \cdot H_2O$: C, 34.54; H, 5.16; N, 10.07; Gd, 22.61. Found: C, 33.97; H, 4.94; N, 9.64: Gd, 22.15.

The relaxation times from a $1.02 \times 10^{-3}M$ solution in 25% $D_2O/H_2O$ in a 90 MHz NMR experiment were determined to be: $T_1 = 201$ msec, $1/T_1 = 4.96$ sec$^1$; $T_2 = 85$ msec; $1/t_2 = 11.8$ sec$^{-1}$. Free metal content (% w/w):0.75%.

EXAMPLE 3 Preparation of (N,N'''-Bis[N-(2,3-dihydroxypropyl)carbamoylmethyl]-diethylenetriamine- N,N',N''-triaceto)iron(III)

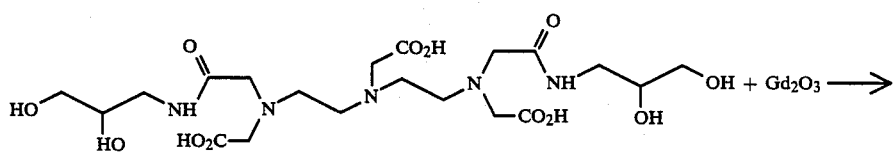

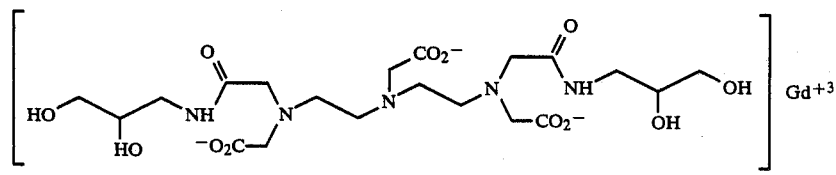

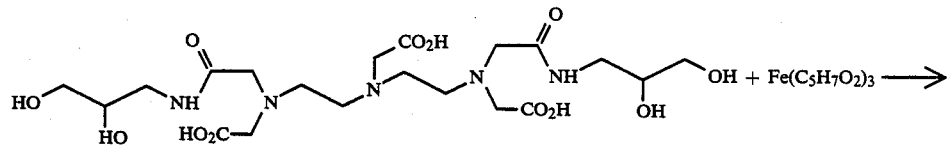

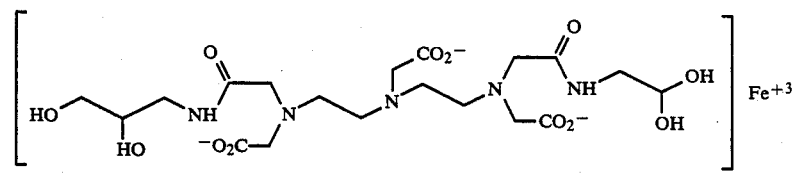

A solution of ferric acetylacetonate (2.52 g; 0.00715 mol) in anhydrous methanol (40 ml) was added to a solution of the ligand N,N'-bis[N-(2,3-dihydroxypropyl)carbamoylmethyl]diethylenetriamine-N,N',N''-triacetic acid (2) (3.86 g, 0.00715 mol) in anhydrous methanol (70 ml). The mixture was stirred at room temperature for 12 hr; then the solvents were removed under reduced pressure. The residue was dissolved in water (60 ml) and extracted two times with ether (50 ml; 25 ml). Then the aqueous phase was evaporated to dryness under reduced pressure to give the iron(III) complex (4) as an orange-brown glass.

Analysis: Calculated for $C_{20}H_{34}N_5O_{12}Fe \cdot H_2O$: C, 39.36; H, 5.62; N, 11.48; Fe, 9.15. Found: C, 39.59; H, 5.77; N, 11.53; Fe, 8.72.

The relxation times from a $1.02 \times 10^{-3}M$ solution in 25% $D_2O/H_2O$ in a 90 MHz NMR experiment were determined to be: $T_1 = 1.07$ sec, $1/T_1 = 0.935$ sec$^{-1}$; $T_2 = 0.211$ sec, $1/T_2 = 4.74$ sec$^1$.

EXAMPLE 4

Preparation of (N,N''-Bis[N-(2,3-dihydroxypropyl)carbamoylmethyl]-diethylenetriamine-N,N'N''-triaceto)manganese(II)

material, and the solvent was removed under reduced pressure. The residue was taken up in the minimum amount of water and applied to a column of "Bio-Rad AG1-X8" resin in the formate form (4.5×30 cm). The column was eluted with water and after a forerun of unreacted 3-amino-1,2-propanediol, the bis amide of ethylenediaminetetraacetic acid was obtained (5.2 g, 56%) as a glass. The material was characterized by $^{13}C$-NMR spectroscopy. The resulting spectrum consisted of 8 lines at 172.9, 169.9, 70.9, 64.1, 57.2, 57.0, 52.2 and 42.7 ppm.

Analysis: Calculated for $C_{16}H_{30}N_4O_{10}$ after correcting for water: C, 43.46; H, 6.84; N, 12.66. Found: C, 43.38; H, 6.56; N, 12.96.

EXAMPLE 6

Preparation of (N,N'-Bis[N-(2,3-dihydroxypropylcarbamoylmethyl]-ethylenediamine-N,N'-diaceto)manganese(II)

A solution of the ligand N,N'-bis[N-(2,3-dihydroxypropyl)carbamoylmethyl]ethylenediamine-N,N'-diacetic acid (3.576 g, 8.16 mmol) in water (30 ml) was treated with manganese carbonate (0.937 g, 8.16 mmol). Water (10 ml) was used to complete the transfer. The

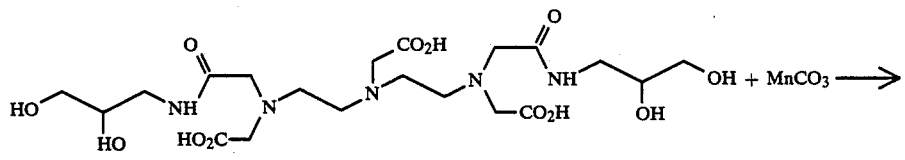

2

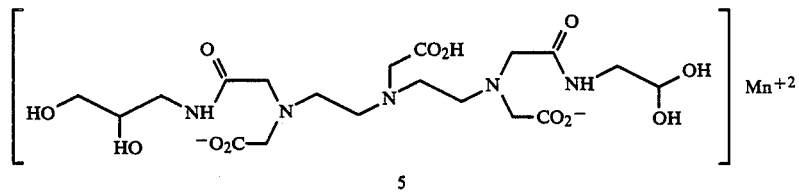

5

To a solution of the ligand N,N''-bis[N-(2,3-dihydroxypropyl)carbamoylmethyl]diethylenetriamine-N,N',N''-triacetic acid (2) (4.5 g, 0.00834 mol) in water (180 ml) was added manganese carbonate (0.96 g; 0.00834 mol) and the mixture was heated at 65° C. for 16 hr. The clear solution was cooled to room temperature and filtered through a 0.45µ Millipore filter. Then the solvent was removed under reduced pressure to give the manganese complex (5) as a slightly yellow glass.

Analysis: Calculated for $C_{20}H_{35}N_5O_{12}Mn \cdot H_2O$: C, 39.35, H, 6.11; N, 11.47; Mn, 8.99. Found: C, 39.11; H, 6.28; N, 11.77; Mn, 9.08.

The relaxation times from a $1.02 \times 10_{-3}M$ solution in 25% Dhd 2O/H$_2$O in a 90 MHz NMR experiment were determined to be: $T_1 = 583$ msec, $1/T_1 = 1.72$ sec ; $T_2 = 111$ msec, $1/T_2 = 9.01$ sec$_{-1}$.

EXAMPLE 5

Preparation of N,N'-Bis[N-(2,3-dihydroxypropyl)carbamoylmethyl]ethylenediamine-N,N'diacetic Acid To a solution of 3-amino-1,2-propanediol (4.1 g, 0.045 mol) in methanol (300 ml) was added ethylenediaminetetraacetic acid anhydride (5.4 g, 0.021 mol). Stirring at room temperature was continued overnight. The mixture was filtered to remove a small amount of insoluble mixture was warmed to 50° C. and was homogeneous after 10 minutes. Heating at 50° C. was continued overnight. The solvent was removed to give the manganese complex of the ligand.

EXAMPLE 7

Acute Intravenous Toxicity Determinations

Acute intravenous toxicity studies were carried out with the complexes of Examples 2, 3 and 4.

Dilutions of each of the complexes were prepared as necessary using Sterile Water for Injection, U.S.P. (Abbott Laboratories, North Chicago, Ill.).

Male and female CFI, SQC strain, albino mice (males, 18.5 to 26.8 g in weight; females 17.4 to 21.6 g in weight) were used. The mice were housed according to standard operating procedures and individually marked with picric acid.

The mice (2 to 4 per dose level) with sexes equally represented received single intravenous injections of the complexes of Examples 2, 3 and 4 via a lateral tail vein at 1.0 ml/min and were observed immediately after dosing and during the 7-day observation period for pharmacotoxic reactions.

Estimated LD$_{50}$ values were calculated with an IBM Personal Computer XT using a modified Behrens-Reed- Muench method (Drug Chem. Toxicol. 4:297–305, 1981).

The $LD_{50}$ of the gadolinium(III) complex of Example 2 (without excess ligand) was determined to be 7.06 mmol/kg. Immediate deaths (<5 min post-injection) were always preceded by convulsions and occurred at dose levels of 8.5, 10.2 and 13.6 mmol/kg. One delayed death occurred at each of 5.1, 6.8 and 8.5 mmol/kg dose groups. Delayed deaths (>4 hr post-injection) were preceded by mild to severe hypoactivity. Changes from initial body weight, at the time of necropsy (7 days), ranged from a loss of 4.4 g (female, 6.8 mmol/kg) to a gain of 1.6 g (male, 6.8 mmol/kg). No gross abnormalities of internal organs or tissues were observed at necropsy of surviving mice.

The $LD_{50}$ of the iron(III) complex of Example 3 (with 15% excess ligand and calcium hydroxide added) was determined to be 5.93 mmol/kg. Convulsions occurred in a majoriyy of the mice immediately following injection of a 0.54M solution of the iron(III) complex at dose levels of 5.4, 8.1 and 10.8 mmol/kg, regardless of whether or not an immediate death resulted thereafter. Most deaths following injection of the iron(III) complex occurred immediately (<1 min post-injection). One delayed death (3 days post-injection) occurred in a male mouse dosed with 8.1 mmol/kg. Surviving mice in the 2.7 and 5.4 mmol/kg groups appeared normal by the end of the 7-day observation period. Changes from initial body weight ranged from a loss of 4.2 g (female, 8.1 mmol/kg) to a gain of 1.3 g (male, 2.7 mmol/kg). No abnormalities were noted upon gross examination of internal organs at necropsy of "found dead" or euthanized mice.

The $LD_{50}$ of the manganese(II) complex of Example 4 (with 15% excess ligand and calcium hydroxide added) was determined to be 12.35 mmol/kg. Convulsions occurred immediately following injection of a 0.68M solution of the manganese(II) complex at all dose levels (6.8, 10.2, 13.6 and 17.0 mmol/kg). Mild-to-moderate hypoactivity was noted in all surviving mice, which, with one exception (female, 13.6 mmol/kg), disappeared within 24 hours. Thereafter, all surviving mice appeared normal. Body weight gains ranged from 1.0 g (female, 13.6 mmol/kg to 4.2 g (male, 10.2 mmol/kg). No abnormalities were noted upon gross examination of internal organs at necropsy of "found dead" or euthanized mice.

As various changes could be made in the above compositions and methods without departing from the scope of the invention, it is intended that all matter contained in the above description shall be interpreted as illustrative and not in a limiting sense.

What is claimed is:

1. A compound of the formula:

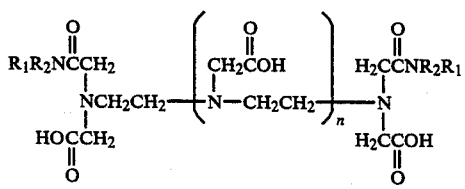

wherein n=0,1, 2, 3, or 4, and $R_1$ is selected from the group consisting of hydrogen and lower alkyl and $R_2$ is a hydroxy lower alkyl group containing between 1 and 6 carbon atoms.

2. A compound as set forth in claim 1 wherein n=1, $R_1$ is hydrogen and $R_2$ is 2,3-dihydroxypropyl.

3. A compound as set forth in claim 1 wherein n=0, $R_1$ is hydrogen and $R_2$ is 2,3-dihydroxypropyl.

4. A compound as set forth in claim 1 which is N,N''-bis[N-(2,3-dihydroxypropyl)carbamoylmethyl]diethylenetriamine-N,N'N''-triacetic acid.

5. A compound as set forth in claim 1 which is N,N''-bis[N-(2,3-dihydroxypropyl)carbamoylmethyl]ethylenediamine-N,N'-diacetic acid.

6. A complex for use in enhancing magnetic resonance images of the body organs and tissues, said complex comprising one or more central metal ions selected from the group consisting of iron(II), iron(III), manganese(II), manganese(III), gadolinium(III), chromium(III), cobalt(II) and nickel(II) and a compound of the formula:

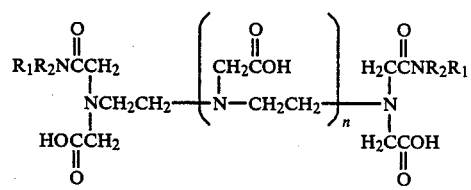

wherein n=0, 1, 2, 3, or 4, and $R_1$ is selected from the group consisting of hydrogen and lower alkyl and $R_2$ is a hydroxy lower alkyl group containing between 1 and 6 carbon atoms.

7. A complex as set forth in claim 6 wherein said central metal ion is iron(III).

8. A complex as set forth in claim 6 wherein said central metal ion is manganese(II).

9. A complex as set forth in claim 6 wherein said central metal ion is gadolinium(III).

10. A complex as set forth in claim 6 which is (N,N''-bis[N-(2,3-dihydroxypropyl)carbamoylmethyl]diethylenetriamine-N,N',N''-triaceto)iron(III).

11. A complex as set forth in claim 6 which is (N,N''-bis[N-(2,3-dihydroxypropyl)carbamoylmethyl]diethylenetriamine-N,N',N''-triaceto)manganese(II).

12. A complex as set forth in claim 6 which is (N,N'-bis[N-(2,3-dihydroxypropyl)carbamoylmethyl]diethylenetriamine-N,N',N''-triaceto)gadolinium(III).

13. A complex as set forth in claim 6 which is (N,N'-bis[N-(2,3-dihydroxypropyl)carbamoylmethyl]ethylenediamine-N,N'-diaceto)manganese(II).

14. A method for enhancing magnetic resonance images of body organs and tissues which comprises administering to a mammal a complex of one or more central metal ions selected from the group consisting of iron(II), manganese(II), manganese(III), gadolinium(III), chromium(III), cobalt(II) and nickel(II) and a compound of the formula:

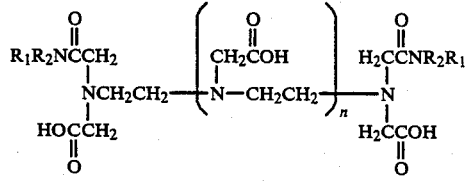

wherein n=0, 1, 2, 3, or 4, and $R_1$ is from the group consisting of hydrogen and lower alkyl and $R_2$ is a hydroxy lower alkyl group containing between 1 and 6 carbon atoms, in a sufficient amount to provide enhancement of magnetic resonance images of said body organs and tissues.

15. A method as set forth in claim 14 wherein said central metal ion is iron(III).

16. A method as set forth in claim 14 wherein said central metal ion is manganese(II).

17. A method as set forth in claim 14 wherein said central metal ion is gadolinium(III).

18. A method as set forth in claim 14 wherein said complex is (N,N''-bis[N-(2,3-dihydroxypropyl)carbamoylmethyl]diethylenetriamine-N,N',N''-triaceto)iron(III).

19. A method as set forth in claim 14 wherein said complex is (N,N''-bis[N-(2,3-dihydroxypropyl)carbamoylmethyl]diethylenetriamine-N,N',N''-triaceto)manganese(II).

20. A method as set forth in claim 14 wherein said complex is (N,N''-bis[N-(2,3-dihydroxypropyl)carbamoylmethyl]diethylenetriamine-N,N',N''-triaceto)gadolinium(III).

21. A method as set forth in claim 14 wherein said complex is (N,N'-bis[N-(2,3-dihydroxypropyl)carbamoylmethyl]ethylenediamine-N,N'-diaceto)manganese(II).

22. A method as set forth in claim 14 wherein magnetic resonance images of the hepatobiliary system are enhanced.

* * * * *